United States Patent [19]

Beyer, Jr.

[11] Patent Number: 4,952,582
[45] Date of Patent: Aug. 28, 1990

[54] PYRAZINOYLGUANIDINE AND DERIVATIVES THEREOF HAVING FEW POLAR SUBSTITUENTS AND BEING USEFUL AS HYPERURETIC AGENTS

[76] Inventor: Karl H. Beyer, Jr., P.O. Box 387, Penllyn, Pa. 19422

[21] Appl. No.: 235,801

[22] Filed: Aug. 23, 1988

Related U.S. Application Data

[63] Continuation of Ser. No. 844,365, Mar. 26, 1986, abandoned, which is a continuation of Ser. No. 336,735, Jan. 4, 1982, Pat. No. 4,594,349.

[51] Int. Cl.$^5$ ........................................... A61K 31/495
[52] U.S. Cl. ..................................................... 514/255
[58] Field of Search .......................................... 514/255

[56] References Cited

U.S. PATENT DOCUMENTS

| | | | |
|---|---|---|---|
| 3,313,813 | 4/1967 | Cragoe | 544/407 |
| 3,345,372 | 10/1967 | Hanifin | 544/406 |
| 4,196,292 | 4/1980 | Woltersdorf | 544/407 |

OTHER PUBLICATIONS

Kubo et al., CA 85:177484s.
*The Journal of General Physiology*, (1976), vol. 68, pp. 43–63, "Effect of Amiloride and Some of its Analogues on Cation Transport in Isolated Frog Skin and Thin Lipid Membranes", Dale J. Benos, et al.
"The Pharmacological Basis of Therapeutics", 7th Edition, Goodman & Gilman, pp. 901–903.
"Physician's Desk Reference", PDR 1987, 41st Edition, pp. 1319–1321.

*Primary Examiner*—Jane T. Fan
*Attorney, Agent, or Firm*—Oblon, Spivak, McClelland, Maier & Neustadt

[57] ABSTRACT

Hyperuretic agents of the formula:

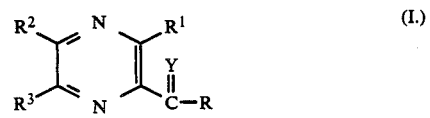

wherein
Y is O or NH;
R is OH; NHCONR$^4$R$^5$; or N=C(NR$^4$R$^5$)$_2$;
R$^1$ and R$^2$ are amino, or mono- or disubstituted amino, provided that R$^1$ and R$^2$ may not both be amino or substituted amino;
and R$^3$ is hydrogen or halo;

enhance renal excretion of urea, thereby lowering plasma urea concentration, and are therefore useful for treating hypertension, eclampsia, uremia, and similar disorders.

17 Claims, No Drawings

PYRAZINOYLGUANIDINE AND DERIVATIVES THEREOF HAVING FEW POLAR SUBSTITUENTS AND BEING USEFUL AS HYPERURETIC AGENTS

This application is a continuation of application Ser. No. 844,365, filed on Mar. 26, 1986, now abandoned, which is a continuation of Ser. No. 336,735, filed Jan. 4, 1982, now U.S. Pat. No. 4,594,349, patented June 10, 1986.

BACKGROUND OF THE INVENTION

1. Field of the Invention

The present invention is concerned with certain pyrazinoic acid derivatives useful as hyperuretic agents, and with pharmaceutical compositions and methods of treating hypertension, eclampsia, uremia, and similar disorders in which the active ingredient employed is one of said pyrazinoic acid derivatives.

In mammals, including man, urea is the principal end product of nitrogen metabolism. Urea is synthesized in the body through the intermediation of the ornithine-urea cycle as from the more toxic ammonia and carbon dioxide. Some twenty-five grams of urea are synthesized in the human body per day and excreted primarily by way of the kidneys.

Urea and sodium (chloride) constitute the principal osmotically active constituents of the body. Whereas this osmotic role is similar for the two, urea and salt, they differ in important respects. Sodium chloride must be obtained from some exogenous source, and the distribution of sodium is essentially limited to extracellular fluid, including plasma water. Urea is synthetized by the body in large amounts, and its distribution is both intracellular and extracellular—being equivalent to total body water. (Potassium serves the intracellular osmotic role assumed by sodium extracellularly.)

When excess sodium is consumed, or retained by less than adequate renal function, iso-osmotic pressure is sustained by thirst-stimulated increased fluid consumption and by fluid retention which may lead to increased blood pressure and/or edema.

In the presence of impaired renal function sufficient to reduce urea excretion, its accumulation may be enough to cause increased intracellular as well as extracellular fluid accumulation, if iso-osmotic relationships are sustained by fluid accumulation. In severe circumstance, uremia may result. It is this intracellular/extracellular accumulation of fluid that is most likely to account for the symptomatology as well as the signs of uremia. At sub-uremic elevations of urea and body water levels the symptomatology may well be confused with salt retention, in which case therapy based on saluresis or hyperuresis may be used interchangeably—to some extent.

The present state of clinical knowledge recognizes that urea is filtered with plasma water at the glomeruli of the kidney and that a portion of that filtered urea undergoes passive back diffusion in the course of urine formation by the nephron. The passive back diffusion of urea can be reduced by increasing the transit rate, i.e., increasing the urine flow.

Increased transit rate can be induced (1) by expanding body fluid volume, which is self-defeating from a therapeutic standpoint; (2) with the aid of an osmotic diuretic, e.g., mannitol, which is impractical because of the need to administer large amounts parenterally, or (3) temporarily, by the use of potent saluretic agents at dosages sufficient to alter electrolyte balance.

In accordance with the present invention, it has been discovered that the mammalian kidney is capable of actively secreting and reabsorbing urea in addition to being filtered at the glomeruli and undergoing passive back diffusion.

Moreover, it has been discovered that the pyrazinoic acid derivatives utilized in the present invention are capable of inhibiting the active renal tubular reabsorption of urea, predominantly; whereas other pyrazinoic acid derivatives such as the fluoro analog of amiloride inhibit preponderantly active tubular secretion of urea without significantly inhibiting active reabsorption of urea. In so doing they lower urea blood levels and increase the osmotic concentration of urine as indications of their capability of influencing osmotically modulated functions of cells and cell membranes. These may thus be called osmoregulatory agents to identify their role in therapy. Their usefulness is considered to extend from the management of mild hypertension to the neurological symptomatology of malignant or severe hypertension, of eclampsia and/or uremia.

2. Brief Description of the Prior Art

Cragoe U.S. Pat. No. 3,313,813 describes 3-amino-5,6-disubstituted-pyrazinoyl guanidines and their use as diuretic, natriuretic agents which selectively enhance the excretion of sodium ions without causing an increase in excretion of potassium 15 ions.

Benos et al. in *V. Gen. Physiol.* 68(1): 43–63 (1976) describe the effect of amiloride and some of its analogs on cation transport in isolated frog skin and thin lipid membranes.

However, none of the above references in any way suggests the use of the particular pyrazinoic acid derivative hyperuretic agents utilized in the present invention for treating hypertension, eclampsia, uremia, and the like, since these references fail to suggest the hyperuretic activity of said pyrazinoic acid derivatives, and since said derivatives do not have sufficient saluretic and antikaluretic activity to be useful in accordance with the requirements described in said references.

DETAILED DESCRIPTION OF THE INVENTION AND PREFERRED EMBODIMENTS

In accordance with the present invention there is provided a pharmaceutical composition for hyperuretic use comprising a pharmaceutically acceptable carrier and a therapeutically effective amount of a compound of the formula:

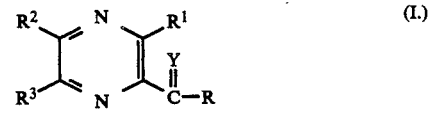

(I.)

wherein
Y is O or NH,
R is OH; NHCONR$^4$R$^5$; or N=C(NR$^4$R$^5$)$_2$; where R$^4$ and R$^5$ are each independently selected from the group consisting of hyrogen; C$_{1-10}$ alkyl, straight or branched chain; aryl C$_{1-4}$ alkyl; mono- or disubstituted aryl C$_{1-4}$ alkyl where the substituents are fluoro, chloro, bromo, iodo, or C$_{1-10}$ alkyl, straight or branched chain;

$R^1$ and $R^2$ are each independently selected from the group consisting of hydrogen, amino, and mono- or disubstituted amino where the substituents are $C_{1-10}$ alkyl, straight or branched chain, or $C_{3-8}$ cycloalkyl; provided that $R^1$ and $R^2$ may not both be amino or substituted amino; and $R^3$ is hydrogen; fluoro; chloro; bromo; or iodo; and a pharmaceutically acceptable salt thereof.

Preferred compounds of the present invention are those of Formula I wherein Y is O or NH; one of $R^1$ and $R^2$ is hydrogen or amino and the other is hydrogen; and $R^3$ is hydrogen.

Particularly preferred compounds of the present invention are the following:
pyrazinoylguanidine;
3-aminopyrazinoylguanidine.

The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanote, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained The pyrazinoic acid derivatives of the present invention possess a high degree of hyperuretic activity. They are of value in the treatment of hypertension. In general they are indicated for a wide variety of conditions where elevated urea levels are manifested. Included within this category are diseases such as eclampsia and uremia.

For these purposes the compounds of the present invention may be administered orally, topically, parenterally, by inhalation spray or rectally in dosage unit formulations containing conventional non-toxic pharmaceutically acceptable carriers, adjuvants and vehicles The term parenteral as used herein includes subcutaneous injections, intravenous, intramuscular, intrasternal injection or infusion techniques In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the active ingredient are employed.

Dosage levels of the order of 25 to 750 mg. per day are useful in the treatment of the above indicated conditions. For example, hypertension is effectively treated by the administration of from about 0.5 to 15 mg. of the compound per kilogram of body weight per day. Advantageously from about 1 to about 15 mg. per kilogram of body weight and especially from about 2 to about 10 mg. per kilogram daily dosage produces highly effective results.

The amount of active ingredient that may be combined with the carrier materials to produce a single dosage form will vary depending upon the host treated and the particular mode of administration. For example, a formulation intended for the oral administration of humans may contain from 25 to 750 mg. of active agent compounded with an appropriate and convenient amount of carrier material which may vary from about 5 to about 95 percent of the total composition. Dosage unit forms will generally contain between from about 25 to about 500 mg. of active ingredient.

It will be understood, however, that the specific dose level for any particular patient will depend upon a variety of factors including the activity of the specific compound employed, the age, body weight general health, sex, diet, time of administration, route of administration, rate of excretion, drug combination and the severity of the particular disease undergoing therapy.

In accordance with the present invention there is further provided a method of treating hypertension comprising administering to a host in need of such treatment a therapeutically effective amount of a compound of the formula:

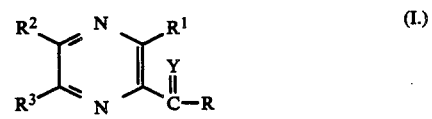

(I.)

wherein Y, R, $R^1$, $R^2$, and $R^3$ have the same meaning as above.

In accordance with the present invention there is still further provided a method of treating a hyperuremic condition comprising administering to a host in need of such treatment a therapeutically effective amout of a compound of the formula:

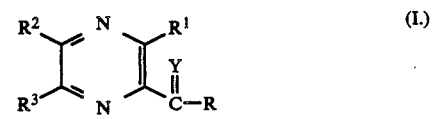

(I.)

wherein Y, R, $R^1$, $R^2$, and $R^3$ have the same meaning as above.

The compounds of the present invention inhibit urea net reabsorption in a dose-related manner that includes increased excretion of sodium, chloride and potassium. Their effect is independent of urine flow, and under conditions where passive back diffusion is minimized they increase urea clearance to approximate glomerular filtration rate.

There is resident in pyrazinoic acid derivatives a variable capability to inhibit secretion of urea into the lumen of the renal tubule. This is minimal in the pyrazinoylguanidine of the present invention, which does not manifest that effect in Dalmatians, whereas the fluoro analog of amiloride almost completely inhibits urea secretion and fluid excretion even when back diffusion is minimized. In stop-flow experiments, inhibition of active reabsorption and secretion can be demonstrated.

The compounds utilized in the present invention are active on oral as well as parenteral administration. 3-Aminopyrazinoylguanidine is most effective promptly, whereas pyrazinoylguanidine effect and blood level requires perhaps an added hour for maximal effect.

As already indicated, the compounds utilized in the present invention may properly be called osmoregulatory agents. Osmoregulation, in turn, involves several interrelated factors.

Salts, as the sum of sodium, chloride and bicarbonate ions, supplies some 93% of the 300 milli Osmols/L of extra-cellular water in humans. Urea supplies about 1.3% of that osmotic force, normally Of the other constituents, only glucose at 1.8% is a factor in osmoregulation.

Thus, osmoregulation of water volume to sustain isotonicity is by thirst and by the action of the antidiuretic hormone on the most distal portion of the nephron to modulate water reabsorption. Whereas there is an appetite for salt regulation, the kidney seems designed to maximize sodium conservation. The search for a salt regulating hormone continues, but the only known "active" sodium reabsorptive mechanisms in the kidney involve the availability of hydrogen ions and/or the aldosterone-modulated availability of potassium for exchange with sodium across the nephron. Sodium rarely becomes a means for increasing water excretion, unless its reabsorption is decreased by the action of natriuretic or saluretic diuretic agents.

One other homeostatic mechanism, the so-called sodium pump, or sodium-potassium-magnesium-dependent ATP-ase mechanism common to cell membranes, serves to relegate the osmoregulatory effect of sodium on fluid volume primarily to extracellular space, or about 25% of total cellular and extra-cellular volume. Thus, exquisitely small increases in sodium retention are capable of expanding extra-cellular volume, thus increasing blood pressure and glomerular filtration rate, without substantial involvement of cell volume.

On the other hand, the osmoregulation of thirst by the cells of the neurohypophysis is not so sensitive to urea concentration. As ADH influences water reabsorption, so does it alter urea back diffusion by the kidney. Conversely, in the course of the human kidney normally excreting some 25 grams of urea per day, that substance serves as the principal osmoregulator of water excretion.

The plasma concentration of urea can be influenced by both protein intake and by renal tubular reabsorption of a portion of the amount filtered by the glomeruli. Thus, a high protein diet normally increases both urea and water excretion. Low protein intake or reduced glomerular filtration rate decreases urea and fluid output. As an approximation, if glomerular filtration rate is reduced to half normal, plasma water concentration of urea will double on a given protein intake. The consequence is to expand intracellular volume as well as extracellular by a ratio of 45:25 or 1.8, assuming a constant osmotic pressure relationship exists between the two spaces. The reason for this important difference between the two spaces is that while sodium is essentially limited to extra-cellular space, urea is distributed more or less uniformly throughout body water. Thus, the patient whose urea plasma concentration is twice normal and whose extracellular volume is expanded carries a greater total expanded volume than if the urea level was normal. What may be considerably more important than the increased total volume is how that increased "intra-cellular" fluid is distributed within the cells, their membranes, the compartmentalization of their structure.

Urea, like salt, is not acutely toxic to the normal subject, if administered with sufficient water to sustain isotonicity. However, the adjustments to marked hyperuremia might be anticipated to include severe imbalance of body fluids, hyponatremia, hypokalemia, edema to which the retention of substances resembling the toxicity of guanidine bases may be thought to contribute to the total but variable clinical picture of uremia.

In view of the foregoing relationship between urea and salt, it should follow that saluretic diuretic therapy would be an adequate control of fluid retention in the absence of hyperuremia. When elevated urea plasma concentration co-exists with fluid retention, or hypertension that responds to thiazide administration, then it would seem rational to induce increased urea excretion—to reduce its blood level.

Increased urea blood level in cardiovascular renal disease is more common than appreciated. Whereas increased urine flow increases urea excretion, diuretics and adrenergic blocking agents are more likely to increase urea blood levels. In view of this proposed reciprocal relationship of salt and urea retention, saluretic diuretic treatment of hypertension represents only half of a rational therapeutic measure—combined saluretic-hyperuremic therapy. In accordance with the present invention, therefore, use of the pyrazinoic acid derivatives described herein makes possible a greater direct control of electrolyte and water balance, i.e., homeostasis, and expands the utility of present therapy by providing direct regulation of tissue fluid as well as extracellular fluid. The present invention provides a new and expanded way of looking at the management of electrolyte and water balance in terms of osmoregulation.

Accordingly, the present invention provides for sustained therapy in the treatment of hypertension; postoperative treatment for the relief of tissue accumulation of fluids without risk of disturbed acid-base balance; and management of acute or chronic hyperuremia that may or may not require occasional dialysis.

The following example, which was actually carried out, will serve to illustrate the hyperuretic activity of the pyrazinoic acid derivatives utilized in the present invention, in contrast to other pyrazinoic acid compounds exemplified by the fluoro analog of amiloride.

EXAMPLE

Food and water were withheld from a female Dalmatian Coach Hound overnight. It was given 4 g of creatinine subcutaneously 20 min. before beginning the first of two successive duplicate 20-min. control clearance periods. Immediately thereafter, a 1.0 ml/min venoclysis of 260 mOsm/L mannitol-PO4 buffer containing the test compound sufficient to sustain an infusion rate of 3.0 mg/kg/h (plus a single 2.0 mg/kg priming i.v. dose) was begun and continued throughout the experiment. Ten minutes later, an additional 1.0 g of creatinine was injected subcutaneously. Creatinine clearance was employed for the measurement of glomerular filtration rate.

Twenty minutes after beginning the venoclysis, the first of a succession of six 20-minute clearances was carried out over the next two hours. Plasma and urine specimens were analyzed for urea, sometimes uric acid, sodium, chloride, potassium, creatinine, and including urine pH and rate of flow.

Pyrazinoylguanidine inhibited the active reabsorption of urea and lowered urea plasma concentration in the Dalmatian, Table I. It lowered the urea plasma concentration and increased the excretion of urea, sodium and potassium, but the effect on chloride excretion was variable. Uric acid excretion was not affected.

When 3-aminopyrazinoylguanidine was administered to a Dalmatian according to the same protocol as for pyrazinoylguanidine, its effect on urea clearance ratio and blood level (Table II) may have been slightly less than for pyrazinoylguanidine (Table I). The natriuretic effects of the two compounds were similar, but pyrazinoylguanidine had a greater kaliuretic effect; that on chloride being more variable among the several dogs and inversely related to urinary pH.

As represented in Table III, the fluoro analog of amiloride profoundly depressed the tubular secretion of urea in the Dalmatian. The effect was immediate and progressed to the point that the concentration of urea in urine was indeterminably low. Urea plasma concentration increased substantially as its excretion was depressed. Although inhibition of active urea secretion into the lumen seemed a likely interpretation of these results, the fluoro analog of amiloride experiment in the Dalmatian was repeated in the presence of sufficient mannitol venoclysis (10%) solution at 5 ml/min) to sustain a urine flow approximately 2.0 ml/min. This urine flow is sufficient to minimize urea back diffusion.

When urine flow was sustained at approximately 2.0 ml/min so as to minimize back diffusion, the fluoro analog of amiloride decreased urea clearance to less than half the control values, Table IV, and urea plasma concentration increased. Although glomerular filtration rate remained steady, uric acid clearance was reduced by the compound to less than half the control values, and its plasma concentration increased slightly. Sodium and chloride excretion increased more than potassium.

The data described above is shown in Tables I–IV below.

TABLE I

| Urine Vol. ml/min | pH | GFR ml/min | UREA P mg % | Clearance ml/min | CR | Na μeq/L | Cl μeq/L | K μeq/L | Urine mOsm/min |
|---|---|---|---|---|---|---|---|---|---|
| "Pyazinoylguanidine effect on endogenous urea, Na, K, Cl excretion by the Dalmation Coach Hound" ||||||||||
| Exp. 7039; Dog Wt. 18.6 kg ||| "Control phase - 260 mOsm/L mannitol-PO4 buffer venoclysis at 1 ml/min" |||||||
| 0.2 | 6.9 | 72.4 | 17.4 | 23.3 | 0.32 | 15 | 19 | 12 | .162 |
| 0.2 | 7.0 | 67.7 | 17.7 | 23.1 | 0.34 | 11 | 13 | 13 | .199 |
| "Pyazinoylguanidine 2 mg/kg I.V. Prime plus 3 mg/kg/h added to manitol venoclysis at 1 ml/min" ||||||||||
| 0.3 | 7.5 | 74.2 | 15.3 | 44.4 | 0.60 | 21 | 18 | 27 | .400 |
| 0.3 | 7.5 | 75.9 | 15.0 | 50.1 | 0.66 | 29 | 20 | 30 | .395 |
| 0.4 | 7.6 | 67.5 | 14.7 | 45.9 | 0.68 | 25 | 24 | 41 | .561 |
| 0.3 | 7.4 | 72.8 | 14.9 | 46.0 | 0.63 | 27 | 24 | 32 | .478 |
| 0.3 | 7.3 | 66.4 | 14.6 | 46.4 | 0.70 | 29 | 18 | 28 | .398 |
| 0.3 | 7.3 | 70.8 | 14.9 | 46.0 | 0.66 | 26 | 17 | 27 | .402 |

TABLE II

| Urine Vol. ml/min | pH | GFR ml/min | UREA P mg % | Clearance ml/min | CR | Na μeq/L | Cl μeq/L | K μeq/L | Uric Acid P mg % | CR |
|---|---|---|---|---|---|---|---|---|---|---|
| "3-Aminopyrazinoylguanidine effect on endogenous urea, Na, K, Cl and uric acid excretion by the Dalmation Coach Hound" |||||||||||
| Exp. 2120; Dog Wt. 14.5 kg ||| "Control phase - 260 mOsm/L mannitol-PO4 buffer venoclysis at 1 ml/min" ||||||||
| 0.2 | 7.2 | 52.2 | 17.6 | 15.6 | 0.33 | 13 | 14 | 18 | 2.2 | 1.28 |
| 0.2 | 7.2 | 50.7 | 18.1 | 17.7 | 0.35 | 12 | 13 | 15 | 2.2 | 1.20 |
| "3-Aminopyrazinoylguanidine 2 mg/kg I.V. Prime plus 3 mg/kg/h added to mannitol venoclysis at 1 ml/min" |||||||||||
| 0.3 | 7.1 | 59.0 | 17.5 | 21.3 | 0.36 | 17 | 15 | 15 | 2.2 | 1.21 |
| 0.3 | 7.0 | 53.3 | 17.1 | 30.4 | 0.57 | 28 | 18 | 13 | 2.1 | 1.13 |
| 0.3 | 7.0 | 57.2 | 17.0 | 41.1 | 0.72 | 26 | 20 | 13 | 2.1 | 1.34 |
| 0.3 | 7.0 | 55.4 | 16.2 | 42.6 | 0.77 | 24 | 21 | 10 | 2.2 | 1.22 |
| 0.4 | 7.1 | 48.9 | 16.4 | 34.6 | 0.71 | 25 | 20 | 13 | 2.0 | 1.34 |
| 0.4 | 7.1 | 53.7 | 16.2 | 37.0 | 0.69 | 24 | 19 | 13 | 2.1 | 1.31 |

TABLE III

| Urine Vol. ml/min | pH | GFR ml/min | UREA P mg % | Clearance ml/min | CR | Na μeq/L | Cl μeq/L | K μeq/L | Urine mOsm/min |
|---|---|---|---|---|---|---|---|---|---|
| "Fluoro analog of amiloride effect on endogenous urea, Na, K, Cl excretion by the Dalmation Coach Hound" ||||||||||
| Exp. 1009; Dog Wt. 18.6 kg ||| "Control phase - 260 mOsm/L mannitol-PO4 buffer venoclysis at 1 ml/min" |||||||
| 0.2 | 7.1 | 76.1 | 22.2 | 26.1 | 0.34 | 20 | 18 | 14 | .276 |
| 0.3 | 7.2 | 74.3 | 22.5 | 26.0 | 0.35 | 20 | 18 | 12 | .307 |
| "Fluoro analog of amiloride 2 mg/kg I.V. Prime plus 3 mg/kg/h added to manitol venoclysis at 1 ml/min" ||||||||||
| 0.1 | 7.6 | 70.2 | 20.2 | 6.2 | 0.09 | 14 | 10 | 1 | .067 |
| 0.1 | 7.7 | 70.8 | 20.4 | 1.6 | 0.02 | 8 | 8 | 1 | .026 |
| 0.1 | 7.8 | 68.6 | 21.4 | 1.2 | 0.02 | 8 | 8 | 1 | .020 |
| 0.1 | 7.8 | 73.7 | 21.7 | 0.4 | 0.01 | 6 | 7 | 1 | .021 |
| 0.2 | 7.8 | 73.3 | 22.5 | 0 | 0 | 6 | 7 | 1 | .038 |
| 0.1 | 7.8 | 67.1 | 23.8 | 0 | 0 | 6 | 7 | 1 | .020 |

TABLE IV

| Urine | | | UREA | | | | | Uric Acid | | |
|---|---|---|---|---|---|---|---|---|---|---|
| Vol. ml/min | pH | GFR ml/min | P mg % | Clearance ml/min | CR | Na μeq/L | Cl μeq/L | K μeq/L | P mg % | CR |
| Fluoro analog of amiloride effect on endogenous urea, Na, K, Cl and uric acid excretion by the Dalmation Coach Hound | | | | | | | | | | |
| Exp. 3140; Dog Wt. 23.6 kg | | | | Control phase - 10% mannitol-PO₄ buffer venoclysis at 5 ml/min | | | | | | |
| 1.9 | 7.1 | 78.4 | 19.6 | 33.0 | 0.42 | 53 | 41 | 23 | 1.60 | 1.08 |
| 2.1 | 7.2 | 77.0 | 19.6 | 31.6 | 0.41 | 63 | 43 | 26 | 1.60 | 1.01 |
| Fluoro analog of amiloride 2 mg/kg I.V. Prime plus 3 mg/kg/h added to mannitol venoclysis at 1 ml/min | | | | | | | | | | |
| 2.1 | 7.3 | 71.3 | 19.3 | 13.5 | 0.19 | 70 | 62 | 29 | 1.65 | 0.61 |
| 1.8 | 7.3 | 75.3 | 20.0 | 9.2 | 0.12 | 70 | 63 | 35 | 1.75 | 0.52 |
| 1.9 | 7.3 | 73.2 | 20.2 | 8.2 | 0.11 | 61 | 76 | 38 | 1.65 | 0.52 |
| 1.7 | 7.4 | 77.5 | 20.8 | 13.3 | 0.17 | 69 | 64 | 29 | 1.75 | 0.49 |
| 1.6 | 7.4 | 71.8 | 21.3 | 12.2 | 0.17 | 72 | 74 | 37 | 1.80 | 0.60 |
| 1.6 | 7.4 | 73.7 | 21.4 | 14.8 | 0.20 | 72 | 80 | 35 | 1.75 | 0.53 |

The pyrazinoic acid derivatives utilized in the present invention may be prepared in accordance with well known procedures, for example those described in U.S. Pat. No. 3,313,813.

What is claimed is:

1. A pharmaceutical composition in unit dosage form useful for treating hypertension or a hyperuremic condition comprising a pharmaceutically acceptable carrier and from about 5 to about 95 percent of the total composition of a compound of the formula;

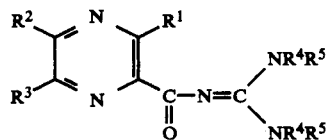

wherein:
R⁴ and R⁵ are each independently selected from the group consisting of hydrogen; $C_{1-10}$ alkyl, straight or branched chain, $C_6$ aryl, $C_{1-4}$ alkyl; mono- or disubstituted $C_6$ aryl $C_{1-4}$ alkyl where the substituents are fluoro, chloro, bromo, iodo, or $C_{1-10}$ alkyl, straight or branched chain;

one of R¹ and R² is, independently, selected from the group consisting of hydrogen, amino, and mono- or disubstituted amino where the substituents are $C_{1-10}$ alkyl, straight or branched chain, or $C_{3-8}$ cycloalkyl; and the other is hydrogen; and R³ is hydrogen;

or a pharmaceutically acceptable salt of said compound.

2. The composition of claim 1 wherein one of R¹ and R² is hydrogen or amino.

3. The composition of claim 1 wherein said compound is pyrazinoylguanidine.

4. The composition of claim 1 wherein said compound is 3-aminopyrazinoylguanidine.

5. The composition of claim 1 wherein said unit dosage contains from 25 to 750 mg of said compound.

6. A pharmaceutical composition useful for treating hypertension or a hyperuremic condition comprising a pharmaceutically acceptable carrier and from about 5 to about 95 percent of the total composition of a compound of the formula:

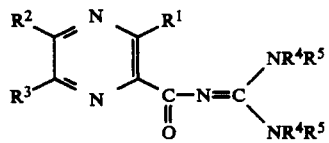

wherein:
R⁴ and R⁵ are each independently selected from the group consisting of hydrogen; $C_{1-10}$ alkyl, straight or branched chain, $C_6$ aryl, $C_{1-4}$ alkyl, mono- or disubstituted $C_6$ aryl $C_{1-4}$ alkyl where the substituents are fluoro, chloro, bromo, iodo, or $C_{1-10}$ alkyl, straight or branched chain;

one of R¹ and R² is, independently, selected from the group consisting of hydrogen, amino, and mono- or disubstituted amino where the substituents are $C_{1-10}$ alkyl, straight or branched chain, or $C_{3-8}$ cycloalkyl; and the other is hydrogen; and R³ is hydrogen;

or a pharmaceutically acceptable salt of said compound.

7. The composition of claim 6 wherein one of R¹ and R² is hydrogen or amino and the other is hydrogen; and R³ is hydrogen.

8. The composition of claim 6 wherein said compound is pyrazinoylguanidine.

9. The composition of claim 6 wherein said compound is 3-aminopyrazinoylguanidine.

10. A pharmaceutical composition in unit dosage form useful for treating hypertension or a hyperuremic condition comprising a pharmaceutically acceptable carrier and from about 5 to about 95 percent of the total composition of a compound of the formula:

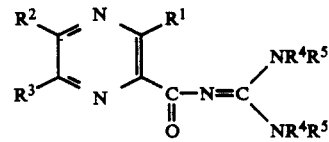

wherein:
R⁴ and R⁵ are each independently selected from the group consisting of hydrogen; $C_{1-10}$ alkyl, straight or branched chain, $C_6$ aryl, $C_{1-4}$ alkyl; mono- or disubstituted $C_6$ aryl $C_{1-4}$ alkyl where the substituents are fluoro, chloro, bromo, iodo, or $C_{1-10}$ alkyl, straight or branched chain;

$R^1$ and $R^2$ are each hydrogen; and $R^3$ is hydrogen: fluoro; chloro; bromo; or iodo;

or a pharmaceutically acceptable salt of said compound.

11. A pharmaceutical composition useful for treating hypertension or a hyperuremic condition comprising a pharmaceutically acceptable carrier and from about 5 to about 95 percent of the total composition of a compound of the formula:

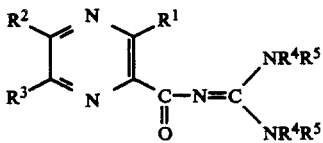

wherein:

$R^4$ and $R^5$ are each independently selected from the group consisting of hydrogen; $C_{1-10}$ alkyl, straight or branched chain, $C_6$ aryl, $C_{1-4}$ alkyl; mono- or disubstituted $C_6$ aryl $C_{1-4}$ alkyl where the substituents are fluoro, chloro, bromo, iodo, or $C_{1-10}$ alkyl, straight or branched chain;

$R^1$ and $R^2$ are each hydrogen; and $R^3$ is hydrogen; fluoro; chloro; bromo; or iodo;

or a pharmaceutically acceptable salt of said compound.

12. A method of treating hypertension comprising administering to a host in need of such treatment a therapeutically effective amount of a compound of the formula:

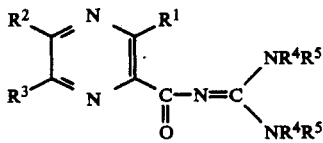

wherein:

$R^4$ and $R^5$ are each independently selected from the group consisting of hydrogen; $C_{1-10}$ alkyl, straight or branched chain, $C_6$ aryl, $C_{1-4}$ alkyl; mono- or disubstituted $C_6$ aryl $C_{1-4}$ alkyl where the substituents are fluoro, chloro, bromo, iodo, or $C_{1-10}$ alkyl, straight or branched chain;

one of $R^1$ and $R_2$ is, independently, selected from the group consisting of hydrogen, amino, and mono- or disubstituted amino where the substituents are $C_{1-10}$ alkyl, straight or branched chain, or $C_{3-8}$ cycloalkyl; and the other is hydrogen; and $R^3$ is hydrogen;

or a pharmaceutically acceptable salt thereof.

13. The method of claim 12 wherein one of R and $R^2$ is hydrogen or amino.

14. The method of claim 12 wherein said compound is pyrazinoylguanidine.

15. The method of claim 12 wherein said compound is 3-aminopyrazinoylguanidine.

16. The method of claim 12 wherein the therapeutically effective amount is from 100 to 1000 mg. per day.

17. A method of treating hypertension comprising administering to a host in need of such treatment a therapeutically effective amount of e compound of the formula:

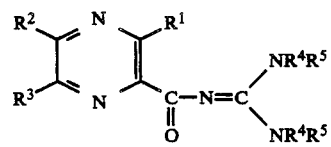

wherein:

$R^4$ and $R^5$ are each independently selected from the group consisting of hydrogen; $C_{1-10}$ alkyl, straight or branched chain, $C_6$ aryl, $C_{1-4}$ alkyl; mono- or disubstituted $C_6$ aryl $C_{1-4}$ alkyl where the substituents are fluoro, chloro, bromo, iodo, or $C_{1-10}$ alkyl, straight or branched chain;

$R^1$ and $R^2$ are each hydrogen; and $R^3$ is hydrogen; fluoro; chloro; bromo; or iodo;

or a pharmaceutically acceptable salt thereof.

* * * * *

UNITED STATES PATENT AND TRADEMARK OFFICE
CERTIFICATE OF CORRECTION

PATENT NO. : 4,952,582
DATED : August 28, 1990
INVENTOR(S) : Karl H. Beyer

It is certified that error appears in the above-identified patent and that said Letters Patent is hereby corrected as shown below:

Column 2, line 29, delete "15".

Column 3, line 38, "thereby obtained" should read

--thereby obtained.--.

Column 6, line 60, "normally Of" should read --normally. Of--.

Column 14, line 24, "amount of e compound" should read

--amount of a compound--.

Signed and Sealed this

Fourth Day of August, 1992

Attest:

DOUGLAS B. COMER

Attesting Officer     Acting Commissioner of Patents and Trademarks